US008986007B2

(12) United States Patent
Chen

(10) Patent No.: US 8,986,007 B2
(45) Date of Patent: Mar. 24, 2015

(54) RESTORABLE ZIRCONIUM DIOXIDE-BASED ONE PIECE DENTAL IMPLANT

(75) Inventor: Chun-Leon Chen, New Taipei (TW)

(73) Assignee: Star Generation Limited, Apia (WS)

( * ) Notice: Subject to any disclaimer, the term of this patent is extended or adjusted under 35 U.S.C. 154(b) by 64 days.

(21) Appl. No.: 13/455,728

(22) Filed: Apr. 25, 2012

(65) Prior Publication Data

US 2012/0225407 A1 Sep. 6, 2012

Related U.S. Application Data

(63) Continuation-in-part of application No. 12/835,136, filed on Jul. 13, 2010, now abandoned.

(51) Int. Cl.
*A61C 8/00* (2006.01)

(52) U.S. Cl.
CPC ............. *A61C 8/0075* (2013.01); *A61C 8/0037* (2013.01); *A61C 8/0024* (2013.01)
USPC ........................................................ 433/174

(58) Field of Classification Search
USPC ........................................ 433/173–176, 201.1
See application file for complete search history.

(56) References Cited

U.S. PATENT DOCUMENTS

| | | | | |
|---|---|---|---|---|
| 1,698,951 A | * | 1/1929 | Holmes | 411/453 |
| 3,590,485 A | * | 7/1971 | Chercheve et al. | 433/174 |
| 4,239,489 A | * | 12/1980 | Ellman et al. | 433/220 |
| 4,259,072 A | * | 3/1981 | Hirabayashi et al. | 433/173 |
| 4,293,302 A | * | 10/1981 | Hassler et al. | 433/173 |
| 4,411,624 A | * | 10/1983 | Ogino et al. | 433/173 |
| 4,424,037 A | * | 1/1984 | Ogino et al. | 433/173 |
| 4,446,579 A | * | 5/1984 | Inamori et al. | 623/11.11 |
| 4,697,969 A | * | 10/1987 | Sparkes | 411/387.7 |
| 4,731,085 A | * | 3/1988 | Koch | 433/173 |
| 4,871,313 A | * | 10/1989 | Maillefer | 433/225 |
| 5,033,999 A | * | 7/1991 | Mersky | 600/25 |
| 5,152,687 A | * | 10/1992 | Amino | 433/173 |
| 5,174,755 A | * | 12/1992 | Fukuda | 433/173 |
| 5,437,551 A | * | 8/1995 | Chalifoux | 433/173 |
| 5,620,323 A | * | 4/1997 | Bressman et al. | 433/174 |
| 5,702,445 A | * | 12/1997 | Brånemark | 606/60 |
| 5,871,359 A | * | 2/1999 | Billet et al. | 433/220 |
| 5,897,319 A | * | 4/1999 | Wagner et al. | 433/174 |
| 6,068,632 A | * | 5/2000 | Carchidi et al. | 606/79 |
| 6,102,702 A | * | 8/2000 | Folsom et al. | 433/172 |
| 6,402,757 B1 | * | 6/2002 | Moore et al. | 606/80 |
| 6,604,945 B1 | * | 8/2003 | Jones | 433/173 |
| 7,338,286 B2 | * | 3/2008 | Porter et al. | 433/173 |

(Continued)

*Primary Examiner* — Cris L Rodriguez
*Assistant Examiner* — Hao D Mai
(74) *Attorney, Agent, or Firm* — Alan D. Kamrath; Kamrath IP Lawfirm, P.A.

(57) ABSTRACT

A restorable zirconium dioxide-based one piece implant includes an implant root made of zirconium dioxide and having a bottom coarse thread portion mounted in a gum of a patient and a top fine thread portion at a top side of the bottom coarse thread portion, an abutment formed integral with a top end of the top fine thread portion of the implant root for mounting a crown, and a vertical center hole extending vertically downwardly from a topmost edge of the abutment into the implant root toward a bottom end of the bottom coarse thread portion of the implant root and having a length greater than ⅔ of the combined length of the implant root and the abutment, so when the abutment breaks, the vertical center hole provides a space for the application of post and core technology to embed a post in the broken abutment to restore the abutment.

2 Claims, 6 Drawing Sheets

(56) References Cited

U.S. PATENT DOCUMENTS

| | | | |
|---|---|---|---|
| 7,396,231 B2 | 7/2008 | Niznick | |
| 7,517,218 B2* | 4/2009 | Hansson | 433/174 |
| 7,677,891 B2* | 3/2010 | Niznick | 433/174 |
| 7,708,738 B2* | 5/2010 | Fourcault et al. | 606/67 |
| 7,785,107 B2* | 8/2010 | Niznick | 433/173 |
| 7,883,336 B2* | 2/2011 | Hansson | 433/173 |
| 8,814,567 B2* | 8/2014 | Zhang et al. | 433/173 |
| 2003/0104338 A1* | 6/2003 | Cottrell | 433/173 |
| 2004/0219488 A1* | 11/2004 | Choi et al. | 433/173 |
| 2005/0136378 A1* | 6/2005 | Ennajimi et al. | 433/173 |
| 2006/0172258 A1* | 8/2006 | Niznick | 433/174 |
| 2006/0199149 A1* | 9/2006 | Niznick | 433/173 |
| 2006/0199150 A1* | 9/2006 | Niznick | 433/173 |
| 2006/0246398 A1* | 11/2006 | Groll et al. | 433/173 |
| 2007/0141535 A1* | 6/2007 | Baldissara | 433/220 |
| 2007/0298379 A1* | 12/2007 | D'Alise | 433/174 |
| 2008/0020348 A1* | 1/2008 | Hansson | 433/173 |
| 2008/0050699 A1* | 2/2008 | Zhang et al. | 433/171 |
| 2008/0081316 A1* | 4/2008 | Chung | 433/174 |
| 2008/0145819 A1* | 6/2008 | Boettcher | 433/174 |
| 2008/0233539 A1* | 9/2008 | Rossler et al. | 433/174 |
| 2008/0261175 A1 | 10/2008 | Hurson | |
| 2009/0061387 A1* | 3/2009 | Lomicka et al. | 433/173 |
| 2009/0061389 A1* | 3/2009 | Lomicka et al. | 433/201.1 |
| 2010/0009316 A1* | 1/2010 | Hurson | 433/173 |
| 2010/0015571 A1* | 1/2010 | Al-Attar | 433/173 |

* cited by examiner

RESTORABLE ZIRCONIUM DIOXIDE-BASED ONE PIECE DENTAL IMPLANT

CROSS-REFERENCE TO RELATED ART

The present invention is a continuation-in-part of U.S. application Ser. No. 12/835,136 filed Jul. 23, 2010 now abandoned, entitled "Restorable one piece implant".

BACKGROUND OF THE INVENTION

1. Field of the Invention

The present invention relates to dental implant technology and more particularly, to a restorable zirconium dioxide-based one piece dental implant.

2. Description of the Related Art

Conventionally, dental implant surgery is to embed an implant into the patient's gum, and then to fasten an abutment to the top side of the implant with a screw, and then to install a crown to the abutment after the wound is healed.

Nowadays, one piece dental implant design is available. A one piece dental implant has the implant and the abutment made in one piece, facilitating dental implant surgery.

Conventional dental implants are commonly prepared by using a titanium-based material. A titanium-based material exhibits an iron-gray color and has a hard texture A titanium-based implant can provide a screw hole for the mounting of a screw to affix an abutment to the top side of the implant. Related dental implant designs are seen in U.S. Pat. No. 7,396,231 entitled "Flared implant extender for endosseous dental implants" and US Application Publication 2008-0261175, entitled "Dental implant".

A new technology is known using zirconium dioxide to prepare a dental implant mating the white color of natural teeth. Since a zirconium dioxide dental implant causes a sense of beauty, it is beginning to be used. However, due to fragile characteristic, a zirconium dioxide-based material cannot be secondarily processed to provide a screw hole for the mounting of a screw to affix an abutment. Thus, a zirconium dioxide-based dental implant can only be made in one piece.

When a zirconium dioxide-based dental implant breaks accidentally or after a long use, the separated crown cannot be used again. When this condition occurs, the residual implant root must be removed from the patient's gum for installation of a new implant. This situation brings great harm and pain to the patient. An improvement in this regard is necessary.

Further, post and core technology has been intensively used in dental surgery. If the tooth structure is insufficient for the installation of a crown due to structural damage, spoil or breaking, post and core technology can be employed to restore the tooth structure for the installation of a crown. However, post and core technology has not yet been used in implant root structure.

SUMMARY OF THE INVENTION

The present invention has been accomplished under the circumstances in view. It is one object of the present invention to provide a restorable zirconium dioxide-based one piece dental implant that is restorable and that reduces patient pain during a dental implant surgery.

To achieve this and other objects of the present invention, a restorable one piece dental implant comprises an implant root, which is made of zirconium dioxide and which comprises a coarse thread portion disposed at the bottom side thereof for installation in the gum of a patient, and a top fine thread portion disposed at the top side of the coarse thread portion, an abutment, which is made of zirconium dioxide and formed integral with one end of the fine thread portion of the implant root remote from the coarse thread portion for the mounting of a crown, and a vertical center hole extending vertically downwardly from the topmost edge of the abutment through the length of the abutment into the implant root to a predetermined depth above the lowest edge of the implant root. The vertical center hole has a length greater than ⅔ of the combined length of the implant root and the abutment. When the abutment breaks accidentally or after a long use, the vertical center hole provides a space for the application of post and core technology to embed a post in the broken abutment in restoring the abutment.

DETAILED DESCRIPTION OF THE PREFERRED EMBODIMENT

Figure 1:
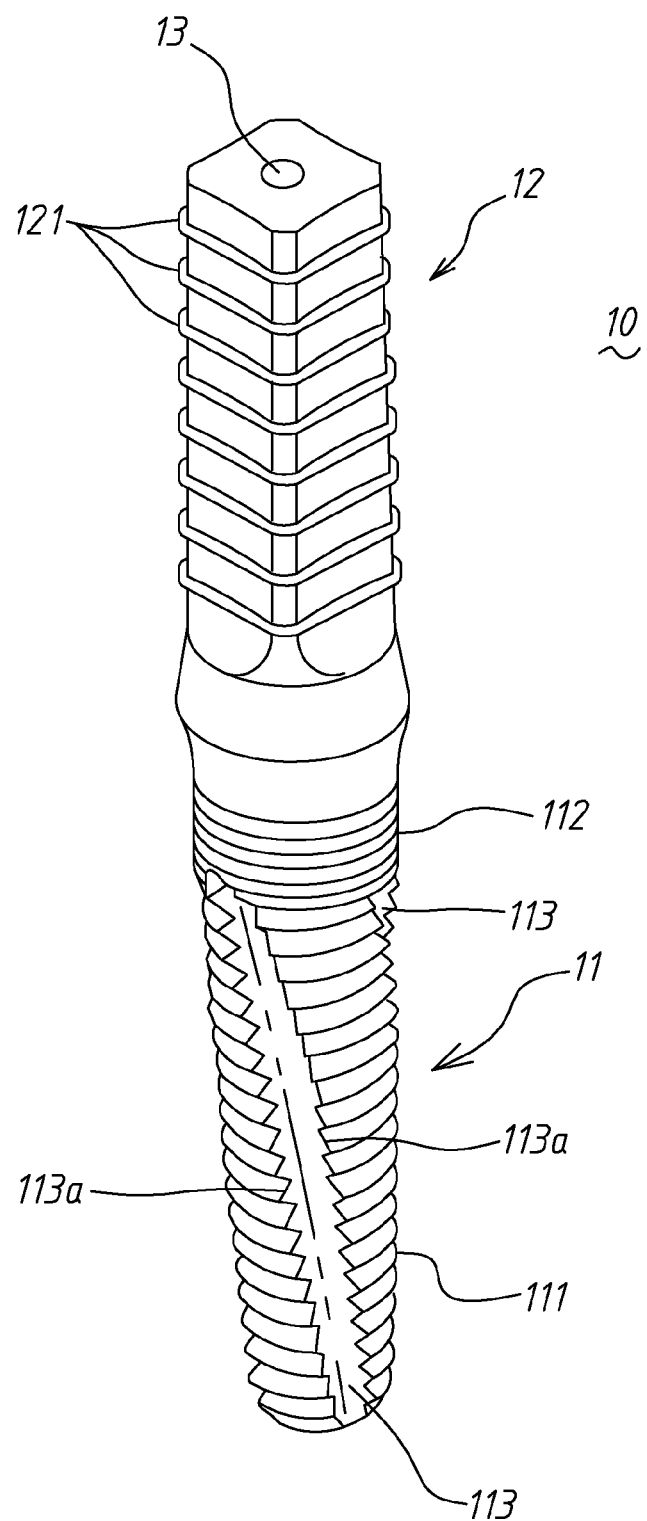
FIG. 1 is an elevational view of a restorable zirconium dioxide-based one piece dental implant in accordance with the present invention.
Figures 2, 2A:
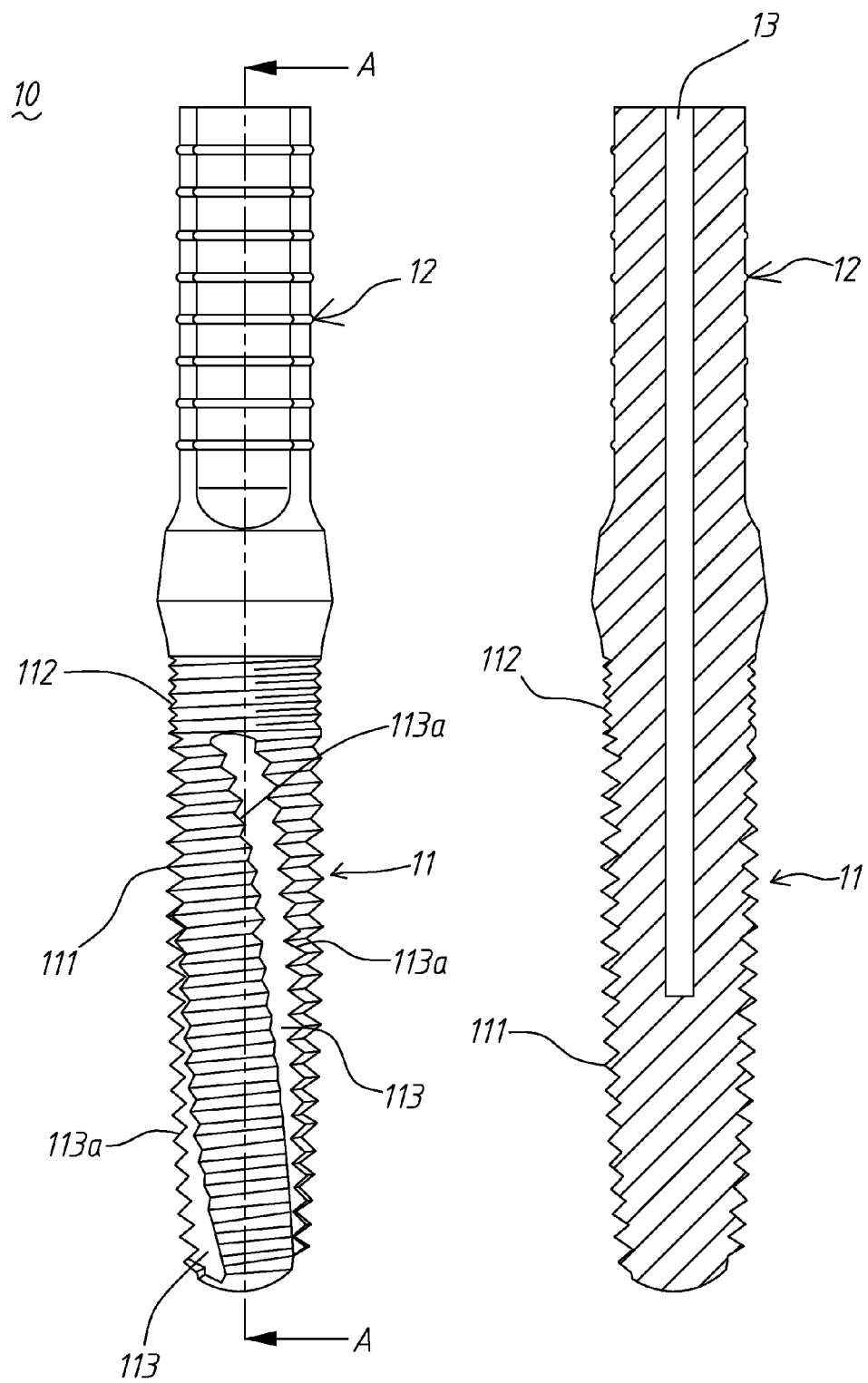
FIG. 2 is a plain view of the restorable zirconium dioxide-based one piece dental implant in accordance with the present invention.
FIG. 2A is a sectional view taken along line A-A of FIG. 2.
Figure 3:
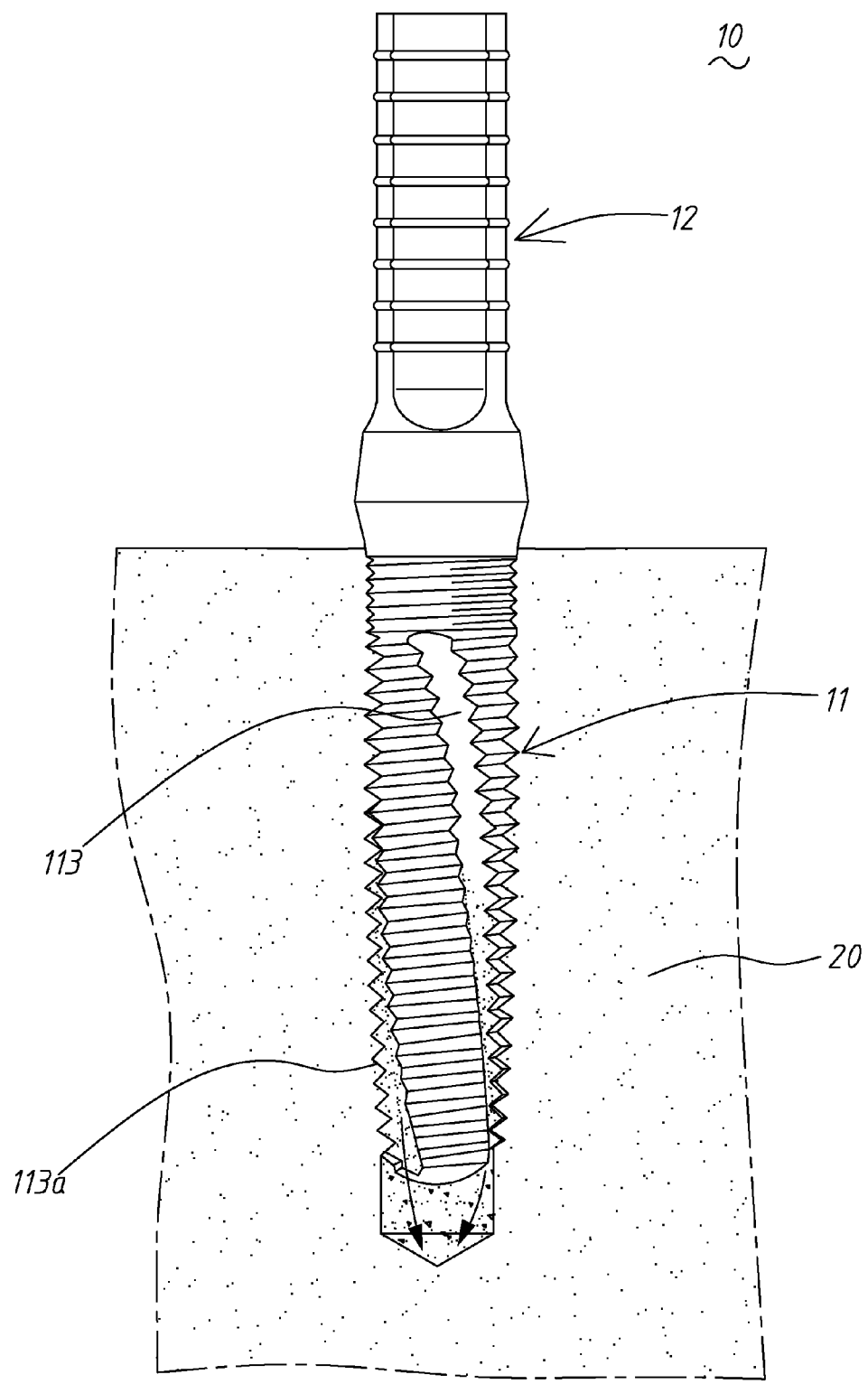
FIG. 3 is a schematic drawing of the present invention, illustrating the restorable zirconium dioxide-based one piece dental implant installed in the gum of a patient.
Figure 4:
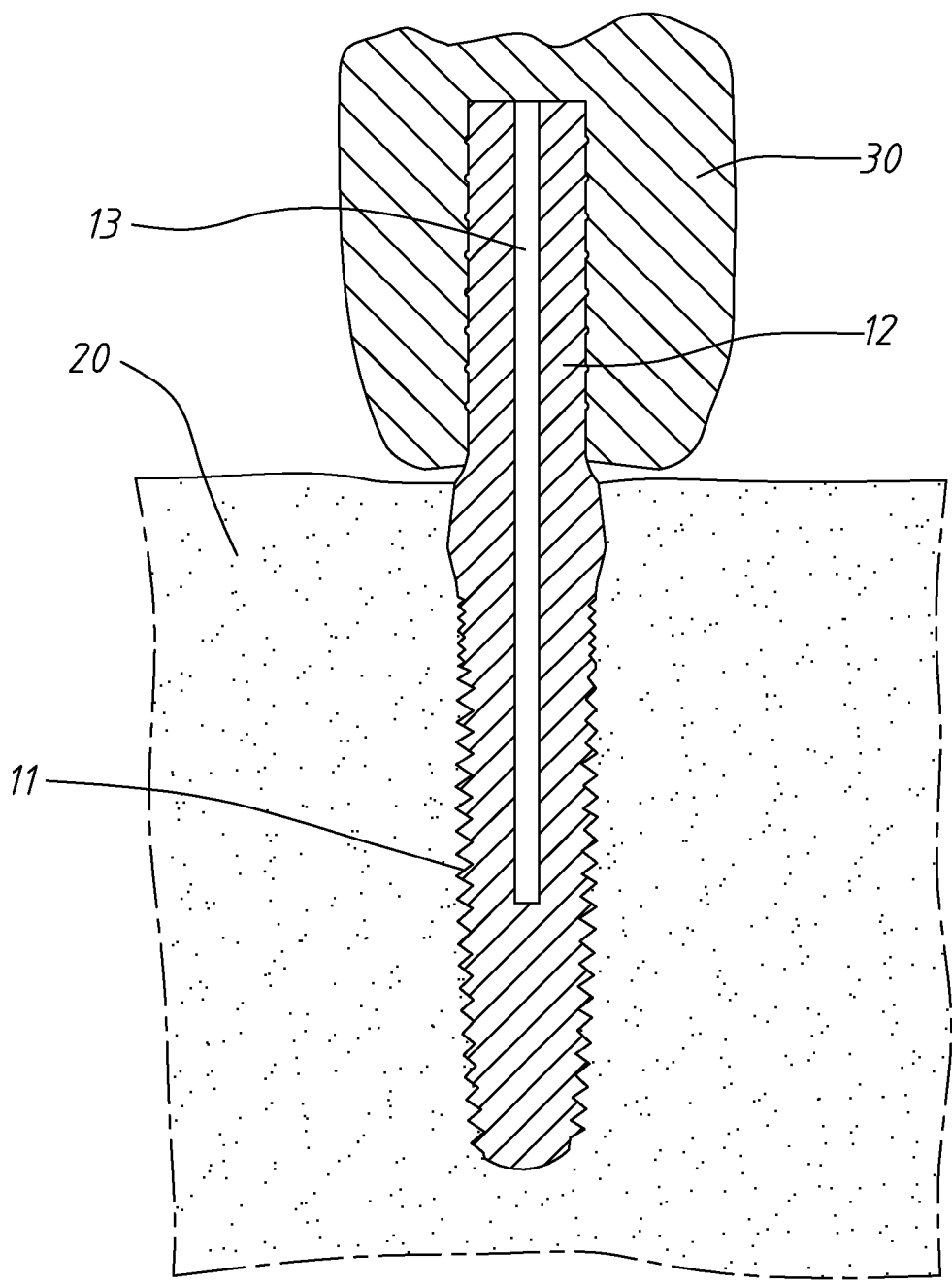
FIG. 4 is a schematic drawing of the present invention, illustrating the restorable zirconium dioxide-based one piece dental implant installed in the gum of a patient and a crown affixed to the abutment of the restorable zirconium dioxide-based one piece dental implant.

Referring to FIGS. 1-3, a restorable zirconium dioxide-based one piece implant 10 in accordance with the present invention is shown. The restorable zirconium dioxide-based one piece implant 10 is prepared by using zirconium dioxide, comprising an implant root 11. The implant root 11 comprises a coarse thread portion 111 at the bottom side that can be driven into the gum of a patient, a fine thread portion 112 at the top side of the coarse thread portion 111, a plurality of spiral grooves 113 spirally cut through the periphery thereof, and a cutting edge 113a longitudinally extending along each of the two opposite lateral sides of each of the spiral grooves 113. The restorable zirconium dioxide-based one piece implant 10 further comprises an abutment 12 formed integral with the top end of the fine thread portion 112 of the implant root 11 for supporting a crown 30, as shown in FIG. 4. The abutment 12 is also prepared by using zirconium dioxide, comprising a plurality of ribs 121 protruded from the periphery thereof and disposed at different elevations.

Referring to FIG. 2A, the restorable zirconium dioxide-based one piece implant 10 further comprises a vertical center hole 13 vertically downwardly extending from the topmost edge of the abutment 12 into the implant root 11 to a predetermined depth close to the bottom end of the implant root 11. Preferably, the vertical center hole 13 has a length greater than ⅔ of the combined length of the implant root 11 and the abutment 12.

When in use, as shown in FIG. 3, a high-speed hand tool is used to drive the implant root 11 into the patient's gum 20. At this time, the cutting edges 113a of the spiral grooves 113 of the implant root 11 cut the bone structure in the gum 20, enabling the separated bone tissues to be propelled toward the inside of the gum 20, as indicated by the arrowhead signs. When matching with sinus lift, the separated bone tissues can be pushed into the sinus cavity. By means of the design of the spiral grooves 113, bone powder can be conveniently filled into the inside of the gum 20 around the implant root 11 during implant surgery, thereby forming a stabilized structure.

After the wound is healed, a crown 30 can then be affixed to the abutment 12, as shown in FIG. 4, finishing the dental implant surgery.

Figures 5, 6:
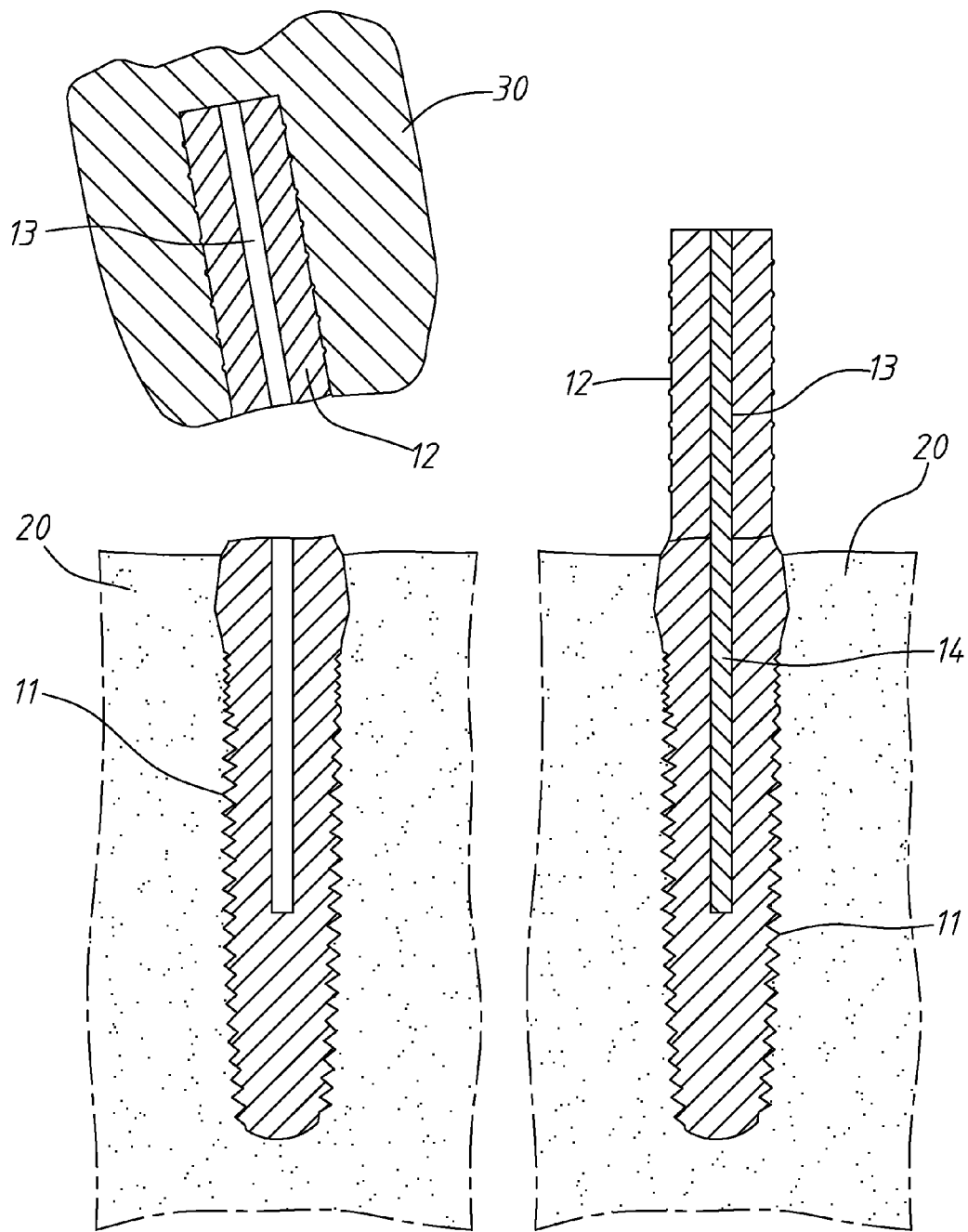
FIG. 5 is a schematic drawing of the present invention, illustrating the abutment of the restorable zirconium dioxide-based one piece dental implant broken.
FIG. 6 is a schematic drawing of the present invention, illustrating the broken restorable zirconium dioxide-based one piece dental implant restored subject to post and core technology.
Figure 7:
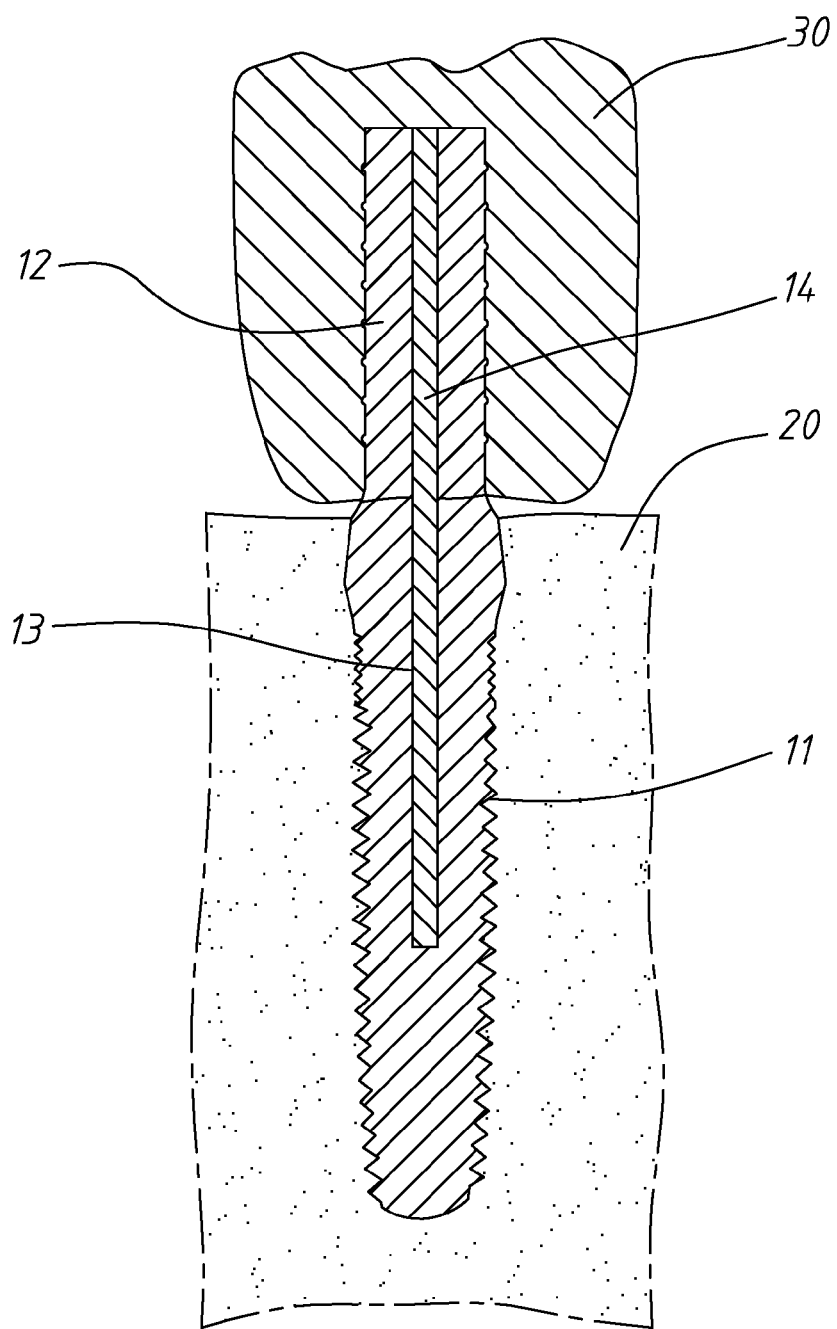
FIG. 7 corresponds to FIG. 6, illustrating a crown affixed to the abutment of the restored zirconium dioxide-based one piece dental implant.

Referring to FIG. 5, after a long use or an improper use of the crown 30, the abutment 11 may break, causing disconnection of the crown 30 from the gum 20. At this time, as shown in FIG. 6, post and core technology can be employed to embed a post 14 in the vertical center hole 13, thereby restoring the abutment 12. Thus, the crown 30 can be affixed to the abutment 12 again, as shown in FIG. 7.

By means of the vertical center hole 13 in the one piece implant 10 and the use of post and core technology, the broken abutment 12 can be restored. Thus, the restorable zirconium dioxide-based one piece implant of the invention shows a better effect when compared to conventional one piece implants. When the restorable zirconium dioxide-based one piece implant is broken, it can be restored without reinstallation of a new implant, reducing patient pain.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A restorable zirconium dioxide-based one piece implant, comprising:
    an implant root made of zirconium dioxide, said implant root comprising a coarse thread portion located at a bottom thereof for installation in a jawbone of a patient, and a fine thread portion located on top of said coarse thread portion;
    an abutment made of zirconium dioxide and integrally formed with said implant root and located on a top of said fine thread portion of said implant root for mounting a crown; said abutment comprises a plurality of ribs protruding outwardly from a periphery thereof, an upper most rib of said plurality of ribs is spaced apart from a topmost edge of said abutment, said fine thread portion of said implant root is located between said plurality of ribs and said coarse thread portion;
    a vertical center hole extending vertically downwardly from said topmost edge of said abutment and through said abutment and extending into said implant root to a predetermined depth above a lowest edge of said implant root, said vertical center hole having a length greater than ⅔ of a combined length of said implant root and said abutment; and
    a post selectively inserted into the vertical center hole during an application of post and core technology in order to restore the abutment in an event that the abutment breaks from the implant root;
    wherein said vertical center hole forms a smooth inner cylindrical wall with a uniform diameter extending along the length thereof, and said post has a corresponding smooth exterior cylindrical surface with a uniform diameter extending along an entire length of said post;
    wherein when said post is inserted into said vertical center hole, said smooth exterior cylindrical surface of the post tightly fits with said smooth inner cylindrical wall of the vertical center hole.

2. The restorable zirconium dioxide-based one piece implant as claimed in claim 1, wherein said implant root comprises a plurality of spiral grooves helically extending around a periphery thereof and extending from a lower portion of said fine thread portion through said course thread portion to said bottom of said implant root, and a cutting edge extending longitudinally along each of two opposite lateral sides of each of said spiral grooves for cutting the bone structures in the gums of the patient for enabling separated bone tissues to be propelled into the gums of the patient when said implant root is being driven into the gum of the patient.

* * * * *